(12) United States Patent
Kawahara (10) Patent No.: US 9,792,261 B2
(45) Date of Patent: Oct. 17, 2017

(54) MEDICAL IMAGE DISPLAY APPARATUS, MEDICAL IMAGE DISPLAY METHOD, AND RECORDING MEDIUM

(71) Applicant: CANON KABUSHIKI KAISHA, Tokyo (JP)

(72) Inventor: Takuto Kawahara, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 365 days.

(21) Appl. No.: 14/043,232

(22) Filed: Oct. 1, 2013

(65) Prior Publication Data

US 2014/0095993 A1    Apr. 3, 2014

(30) Foreign Application Priority Data

Oct. 2, 2012 (JP) .................................. 2012-220670

(51) Int. Cl.
*G06F 19/00* (2011.01)
*G06F 17/21* (2006.01)

(52) U.S. Cl.
CPC .......... *G06F 17/212* (2013.01); *G06F 19/321* (2013.01); *G06F 19/3406* (2013.01)

(58) Field of Classification Search
CPC .... G06F 17/212; G06F 17/211; G06F 19/321; G06F 19/3406
USPC ................................................ 715/273, 730
See application file for complete search history.

(56) References Cited

U.S. PATENT DOCUMENTS

| | | | | |
|---|---|---|---|---|
| 7,965,907 B2* | 6/2011 | Takekoshi | ............... | G06Q 10/10 358/403 |
| 8,334,878 B2* | 12/2012 | Moriya | ................. | G06F 19/321 345/619 |
| 2006/0072700 A1* | 4/2006 | Chen | ...................... | A61B 6/032 378/4 |
| 2009/0022378 A1* | 1/2009 | Nemoto | ................. | A61B 6/032 382/131 |
| 2009/0054755 A1* | 2/2009 | Shiibashi | .............. | G06F 19/321 600/407 |
| 2009/0123892 A1* | 5/2009 | Sogo | ....................... | A61C 11/00 433/213 |
| 2009/0232369 A1* | 9/2009 | Senegas | ................ | G06T 7/0012 382/128 |
| 2010/0053213 A1* | 3/2010 | Ishida | ................... | G06F 19/321 345/629 |
| 2010/0119129 A1* | 5/2010 | Moriya | ................. | G06T 7/0081 382/128 |
| 2010/0122206 A1* | 5/2010 | Matsue | ............. | H04N 1/00344 715/785 |

(Continued)

FOREIGN PATENT DOCUMENTS

CN    1702645 A    11/2005
CN    102415896 A    4/2012
(Continued)

*Primary Examiner* — Scott Baderman
*Assistant Examiner* — Hassan Mrabi
(74) *Attorney, Agent, or Firm* — Canon U.S.A., Inc. IP Division (57) ABSTRACT

A medical image display apparatus determines a priority order of each of medical image data based on a display direction of a body model and an imaging direction of the medical image data. The medical image display apparatus displays each of the medical image data on the body model according to the priority order of the medical image data.

14 Claims, 8 Drawing Sheets

(56) References Cited

U.S. PATENT DOCUMENTS

| | | | | |
|---|---|---|---|---|
| 2010/0177945 A1* | 7/2010 | Moriya | ............ | G06T 7/606 |
| | | | | 382/131 |
| 2010/0189322 A1* | 7/2010 | Sakagawa | ......... | G06F 19/321 |
| | | | | 382/128 |
| 2011/0194744 A1* | 8/2011 | Wang | ............ | G06F 19/3437 |
| | | | | 382/131 |
| 2012/0162222 A1* | 6/2012 | Zaiki | ............ | A61B 6/504 |
| | | | | 345/419 |
| 2012/0253170 A1* | 10/2012 | Kim | ............ | A61B 19/50 |
| | | | | 600/410 |

FOREIGN PATENT DOCUMENTS

| CN | 102573635 A | 7/2012 |
|---|---|---|
| JP | 2008-250897 A | 10/2008 |
| JP | 2008-264167 A | 11/2008 |

\* cited by examiner

MEDICAL IMAGE DISPLAY APPARATUS, MEDICAL IMAGE DISPLAY METHOD, AND RECORDING MEDIUM

BACKGROUND

Field

Aspects of the present invention generally relate to a technique for displaying medical image data.

Description of the Related Art

In recent years, a medical image diagnostic apparatus has been developed, and a medical image has been essential for making a pathological diagnosis in a medical field. The number of sites, which can be imaged, and the frequency of the imaging have increased. Thus, the number of medical images to be handled is continuing to increase. Usually, a huge number of medical images have been stored in an image server inside or outside a hospital. A doctor in charge has interpreted a medical image by reading out the medical image using a medical image display apparatus connected to an image server via a network. The medical image is used not only at the time of diagnosis but also as explanatory materials for an explanation of an inspection result to a patient (an informed consent) and a medical conference and at the time of conference presentation. It takes a very long time to find out required information from the huge number of medical images.

To reduce such a burden on the doctor, Japanese Patent Application Laid-Open No. 2008-264167 discusses a technique for improving working efficiency by displaying a list of medical images to be capable of visually determined what type of attribute the displayed list has. Japanese Patent Application Laid-Open No. 2008-250897 discusses a technique for enabling a diagnosis result and a method of treatment to be simply explained by overlaying and displaying a detailed view of a site of the body, on which a pointer has been overplayed, on an appearance view of the site.

However, in the technique discussed in Japanese Patent Application Laid-Open No. 2008-264167, while attribute information of the medical image can be graphically displayed using a site image of each of sites obtained by dividing the body, the site recorded on the medical image cannot be specifically displayed. Only information added to the medical image is displayed. Thus, unless the medical image is opened, the medical image cannot be confirmed. In the technique discussed in Japanese Patent Application Laid-Open No. 2008-250897, the medical image is overlaid and displayed on the appearance view of the site of the body. Thus, while the site recorded on the medical image can be intuitively grasped, the technique does not consider searching for the required medical image from among the huge number of medical images.

SUMMARY

Aspects of the present invention are generally directed to intuitively grasping respective imaging sites of medical image data, and making the required medical image data efficiently selectable.

According to an aspect of the present invention, a medical image display apparatus includes a display control unit configured to display each of medical image data at a position on a body model corresponding to a respective imaging site of each of the medical image data, and a determination unit configured to determine a priority order of each of the medical image data based on a display direction of the body model and an imaging direction of each of the medical image data, in which the display control unit displays each of the medical image data on the body model according to the priority order of each of the medical image data.

Further features of the present disclosure will become apparent from the following description of exemplary embodiments with reference to the attached drawings.

BRIEF DESCRIPTION OF THE DRAWINGS

FIGS. 3A, 3B, 3C, and 3D respectively illustrate examples of screens of an inspected image area in the first exemplary embodiment.

DESCRIPTION OF THE EMBODIMENTS

Various exemplary embodiments, features, and aspects of the embodiments will be described in detail below with reference to the drawings.

Figure 1:
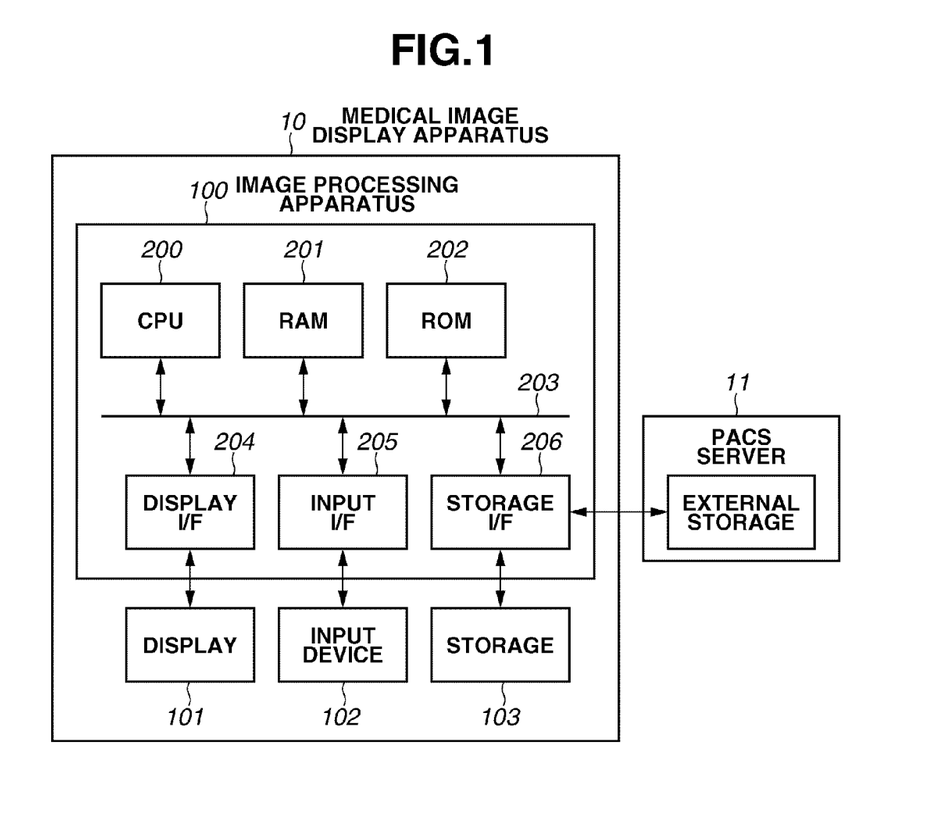
FIG. 1 illustrates a configuration of a medical image display apparatus 10 according to a first exemplary embodiment.

A first exemplary embodiment will be described below. FIG. 1 illustrates a configuration of a medical image display apparatus 10 according to the first exemplary embodiment. In FIG. 1, a central processing unit (CPU) 200 integrally controls devices connected via a bus 203. The CPU 200 temporarily reads out an operation system (OS) and a program and data related to processing characteristic of the present exemplary embodiment to a random access memory (RAM) 201 from a read-only memory (ROM) 202 or a storage 103 connected via a storage interface (I/F) 206, and executes the read program and data.

The RAM 201 is used as a main memory or a work area of the CPU 200 that can be accessed at high speed. A display I/F 204 converts image data generated within the image processing apparatus 100 into a signal that can be processed in a display 101. An input I/F 205 accepts input corresponding to an operation performed by a user with an input device 102 such as a keyboard or a mouse. The storage I/F 206 performs conversion processing between a data format, which can be used within an image processing apparatus 100, and a data format used for storage in the storage 103.

The storage 103 is a hard disk drive device to be loaded into the medical image display apparatus 10. In many medical fields, a picture archiving and Communication System (PACS) may retain medical image data obtained by the medical image display apparatus 10. In the present exemplary embodiment, the medical image display apparatus 10 is also connected to a PACS server 11. The medical image data is stored in an external storage within the PACS server 11, and is browsed by the medical image display apparatus 10. However, the medical image data may be stored in the storage 103, and may be readable by the image processing apparatus 100 using the storage I/F 206, various types of network I/Fs, or an external memory I/F.

Figure 2:
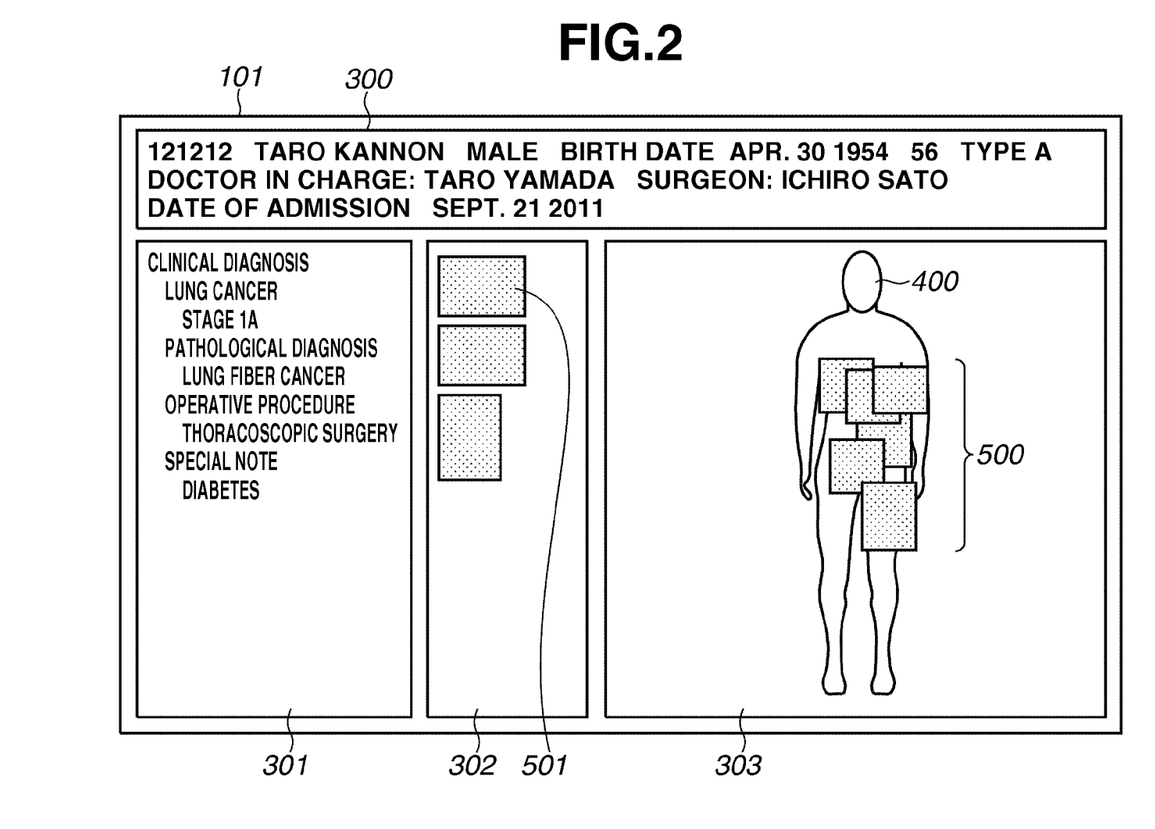
FIG. 2 illustrates an example of display of image data on a display.

FIG. 2 illustrates an example of display of image data on the display 101. The present exemplary embodiment assumes a use case for designating, out of medical image data of a subject (patient) to be discussed in a medical conference, the required medical image data in a stage of preparing to make materials for the medical conference.

A patient information area 300 where basic information of a patient is displayed is provided in an upper part of a display unit of the display 101. In the patient information area 300, the name, a picture, the gender, the age, the blood type, and a doctor in charge of the patient are displayed. At the left of the display unit of the display 101, a medical information area 301 where medical information of the patient is displayed is provided. In the medical information area 301, a case history up to the present date, diagnosis information, and an operative procedure are displayed. At the right of the medical information area 301, a designated image area 302 is provided. In the designated image area 302, medical image data, which have been designated out of many medical image data, such as medical image data used and image data to be compared with the medical image data when grounds based on which the operative procedure has been determined are described in the medical conference are displayed. At the right of the designated image area 302, an inspected image area 303 is provided. Reduced medical image data 500 are displayed in the inspected image area 303. More specifically, the medical image data 500, which have been read from the PACS server 11 via the storage I/F 206 and reduced, are displayed in the inspected image area 303. When the desired medical image data 500 is designated out of the medical image data 500, which have been displayed in the inspected image area 303, the designated medical image data 500 is stored in the designated image area 302.

FIGS. 3A, 3B, 3C, and 3D respectively illustrate examples of screens of the inspected image area 303 in the first exemplary embodiment. A method for displaying a body model 400 and medical image data 500 will be described below with reference to FIGS. 3A, 3B, 3C, and 3D.

FIG. 3A illustrates an example of an initial screen of the inspected image area 303. The body model 400 is displayed in the inspected image area 303. Each of the medical image data 500 is given an imaging site where the medical image data is imaged, and is superimposed and displayed at a position, which corresponds to the imaging site, on the body model 400. While the entire body model 400 is displayed on the initial screen in the examples illustrated in FIGS. 3A, 3B, 3C, and 3D, a part of the body model 400 may be displayed if all the medical image data 500 can be displayed. In the present exemplary embodiment, any position on the medical image data 500 can be set as an imaging site. If an important target site such as a tumor exists within the medical image data 500, the target site can be set as an imaging site of the medical image data 500.

In the present exemplary embodiment, a priority order of each of the medical image data 500 is determined by comparing a display direction of the body model 400 and an imaging direction of the medical image data 500. In the inspected image area 303 illustrated in FIG. 2, for example, the body model 400 is displayed from the front. Thus, a high priority order is determined for the medical image data 500, which has been imaged from the front, out of the medical image data 500 displayed on the body model 400. The priority order of each of the medical image data 500 may be determined in consideration of the imaging date of the medical image data 500, the update date of the medical image data 500, and the type of a medical imaging apparatus that has imaged the medical image data 500 in addition to the imaging direction of the medical image data 500. When the priority order is determined, a result of a computer aided diagnosis (CAD) for supporting a diagnosis by a doctor may be considered. In the present exemplary embodiment, the higher priority order the medical image data 500 has, the more forward the medical image data 500 is brought to the front. However, the higher priority order the medical image data 500 has, the larger the medical image data 500 may be displayed. Alternatively, the color of a visible outline of the medical image data 500 may be changed according to the priority order.

FIGS. 3B to 3D respectively illustrate examples of screens of the inspected image area 303 when a movement operation of the body model 400 has been performed from the initial screen of the inspected image area 303 illustrated in FIG. 3A. While an example in which the mouse and the keyboard (not illustrated) serving as the typical input device are used to perform the movement operation will be described, the present embodiment is not limited to this. The body model 400 may be operated using another input device such as a touch panel.

FIG. 3B illustrates an example of display of the screen of the inspected image area 303 when the body model 400 has been moved leftward from the initial screen of the inspected image area 303 illustrated in FIG. 3A. A user clicks a left button of the mouse while a pointer is displayed within the inspected image area 303, except on the medical image data 500, and drags the mouse leftward while pressing a ctrl key on the keyboard. Thus, the body model 400 can be moved leftward.

FIG. 3C illustrates an example of display of the screen of the inspected image area 303 when the body model 400 has been enlarged from the initial screen of the inspected image area 303 illustrated in FIG. 3A. The user clicks a right button of the mouse while the pointer is displayed within the inspected image area 303, except on the medical image data 500, and drags the mouse upward while pressing the ctrl key on the keyboard. Thus, the body model 400 can be enlarged.

FIG. 3D illustrates an example of display of the screen of the inspected image area 303 when the body model 400 has been rotated around a body trunk of the body model 400 so that the front of the body is directed rightward from the initial screen of the inspected image area 303 illustrated in FIG. 3C. The user simultaneously clicks the right and left buttons of the mouse while the pointer is displayed within the inspected image area 303, except on the medical image data 500, and drags the mouse rightward while pressing the ctrl key on the keyboard. Thus, the body model 400 can be rotated.

When the body model 400 is rotated, a display direction of the body model 400 is changed, so that the priority order of each of the medical image data 500 is changed. Medical image data 501 illustrated in FIGS. 3C and 3D is medical image data recorded from the front (a front view), and is given information imaged from the front (specifically, information representing a vector that points an imaging site from the front). Medical image data 502 illustrated in FIGS. 3C and 3D is medical image data recorded from the side (a side view), and is given information imaged from the side (specifically, information representing a vector that points an imaging site from the right side).

In FIG. 3C, the body model 400 is displayed from a front surface direction. Thus, the medical image data (front view) 501 is displayed in front of the medical image data (side view) 502. In FIG. 3D, the body model 400 is displayed from a side surface direction. Thus, the medical image data (side view) 502 is displayed in front of the medical image data (front view) 501.

While an example of rotation around the body trunk has been illustrated, the present embodiment is not limited to this. Stereoscopic rotation including a direction perpendicular to the body trunk is also included. Thus, the body model 400 can be displayed in an omnidirectional manner. For example, the body model 400 is displayed from the top of the head or from a diagonal direction behind the vicinity of the shoulder. Thus, the present embodiment can also be applied to medical image data of an apparatus capable of imaging image data from a free angle such as image data obtained by capturing a three-dimensional image, which has been synthesized from a series of slice images such as a computer tomography (CT) and a magnetic resonance imaging (MRI), and image data obtained by imaging a skin surface used in dermatology and cosmetic surgery using a digital camera or the like.

Figure 4A:
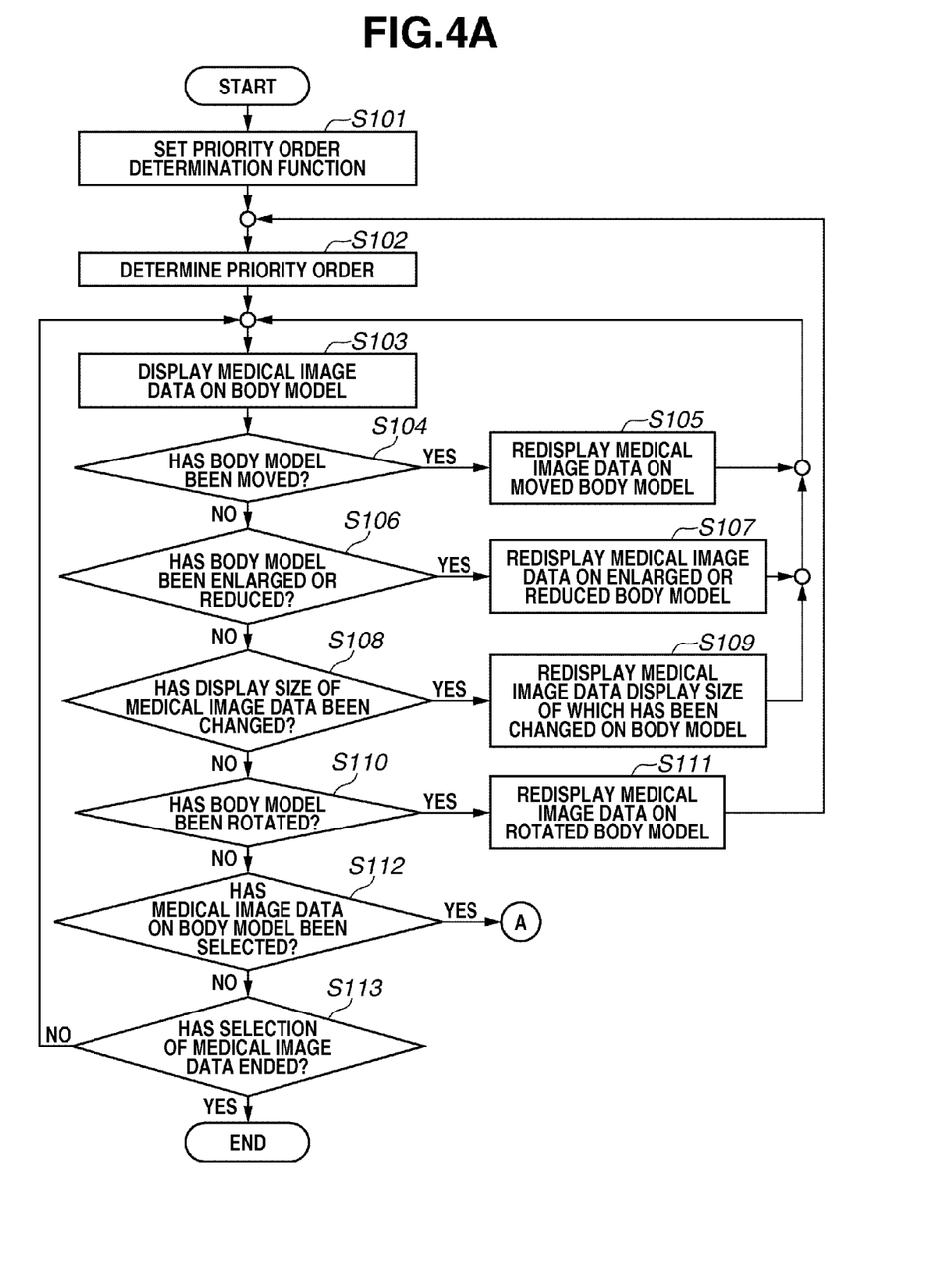
FIGS. 4A and 4B are flowcharts illustrating processing of a medical image display apparatus according to the first exemplary embodiment.
Figure 4B:
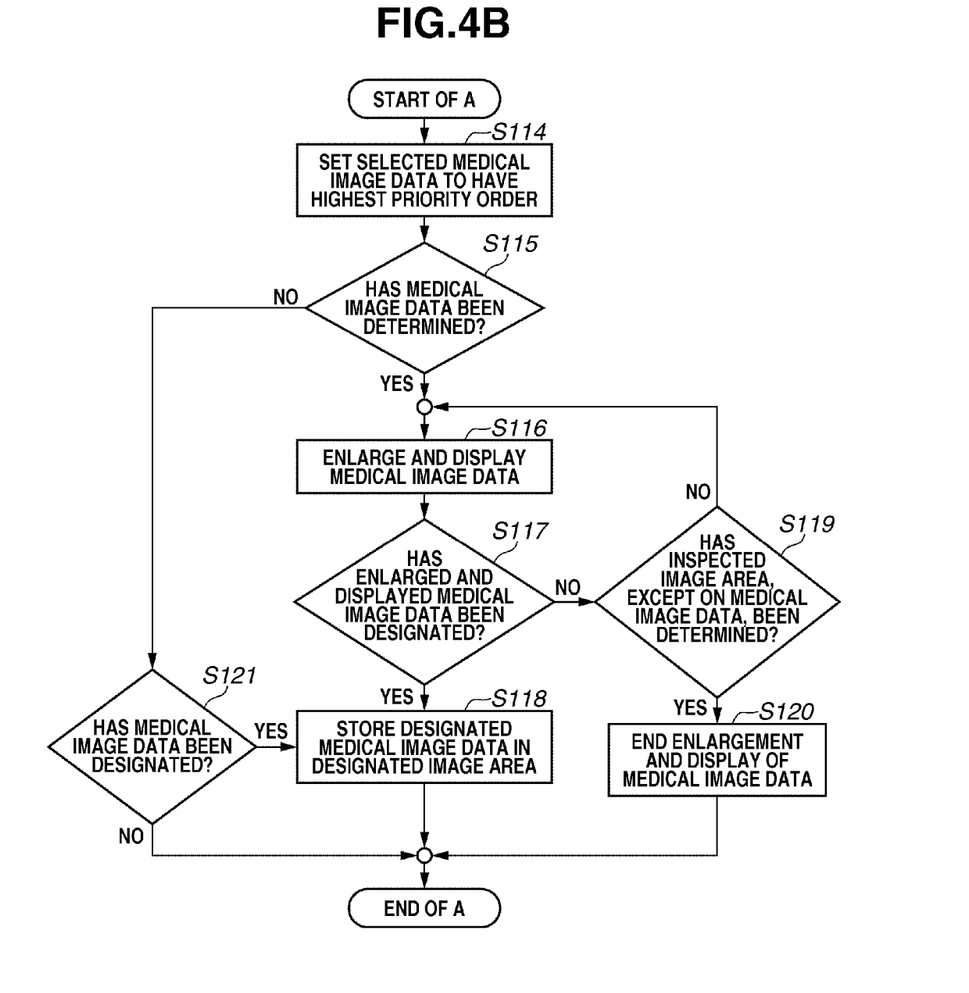

FIGS. 4A and 4B are flowcharts illustrating processing of the medical image display apparatus 10 according to the first exemplary embodiment. More specifically, FIG. 4A illustrates processing performed when a movement operation of a body model 400 has been performed, and FIG. 4B illustrates processing for medical image data 500, which has been designated in the inspected image area 303, to be stored in the designated image area 302. The processing steps illustrated in FIGS. 4A and 4B are implemented when the CPU 200 reads out a required program and data from the recording medium such as the ROM 202 to the RAM 201 and executes the read program and data.

In step S101, the CPU 200 sets a function of determining a priority order of each of medical image data 500. More specifically, when determining the priority order, the CPU 200 sets which of an imaging direction of the medical image data 500, an imaging date of the medical image data 500, an update date of the medical image data 500, the type of the medical image display apparatus 10 that has imaged the medical image data 500, and a result of a CAD is to be emphasized to determine the priority order. The setting is performed according to an operation performed by a user. If the priority order determination function is not changed, the priority order determination function previously set is directly diverted.

In step S102, the CPU 200 determines the priority order of each of the medical image data 500 using the priority order determination function, which has been set in step S101. In step S103, the CPU 200 displays the medical image data 500 on the body model 400 according to the determined priority order. In step S104, the CPU 200 determines whether the body model 400 has been moved. If the body model 400 has been moved (YES in step S104), the processing proceeds to step S105. On the other hand, if the body model 400 has not been moved (NO in step S104), the processing proceeds to step S106.

In step S105, the CPU 200 redisplays the medical image data 500 on the moved body model 400. In step S106, the CPU 200 determines whether the body model 400 has been enlarged or reduced. If the body model 400 has been enlarged or reduced (YES in step S106), the processing proceeds to step S107. On the other hand, if the body model 400 has not been enlarged or reduced (NO in step S106), the processing proceeds to step S108.

In step S107, the CPU 200 redisplays the medical image data 500 on the enlarged or reduced body model 400. In step S108, the CPU 200 determines whether the display size of the medical image data 500, which has been displayed on the body model 400, has been changed. If the display size of the medical image data 500 has been changed (YES in step S108), the processing proceeds to step S109. On the other hand, if the display size of the medical image data 500 has not been changed (NO in step S108), the processing proceeds to step S110.

In step S109, the CPU 200 redisplays the medical image data 500, the display size of which has been changed, on the body model 400. In step S110, the CPU 200 determines whether the body model 400 has been rotated. If the body model 400 has been rotated (YES in step S110), the processing proceeds to step S111. On the other hand, if the body model 400 has not been rotated (NO in step S110), the processing proceeds to step S112.

In step S111, the CPU 200 redisplays the medical image data 500 on the rotated body model 400. The rotation of the body model 400 may be detected by a change in a display direction of the body model 400. If the display direction of the body model 400 has been changed, the priority order of each of the medical image data 500 is changed according to the change. Therefore, each of the medical image data 500 is redisplayed at a position according to the changed priority order on the rotated body model 400.

In step S112, the CPU 200 determines whether the medical image data 500 has been selected according to an operation performed by the user. If the medical image data 500 has been selected (YES in step S112), the processing proceeds to step S114. On the other hand, if the medical image data 500 has not been selected (NO in step S112), the processing proceeds to step S113. In step S113, the CPU 200 determines whether the user has input the end of the selection of the medical image data 500. If the end of the selection of the medical image data 500 has been input (YES in step S113), the processing ends. On the other hand, if the end of the selection of the medical image data 500 has not been input (NO in step S113), the processing proceeds to step S103.

In step S114, the CPU 200 sets the medical image data 500, which has been selected in step S112, to have the highest priority order. By doing this, even if the selected medical image data 500 is hidden on the back of the medical image data 500, the selected medical image data 500 can be displayed on a forefront surface. Thus, the entire area of the medical image data 500 can be confirmed. A method for selecting the medical image data 500 in step S112 is performed by one-clicking the left button of the mouse on the medical image data 500 to be a target, for example. In addition, the method for selecting the medical image data 500 may be performed by right-clicking the mouse in the inspected image area 303 to display a list of the medical image data 500 and selecting the medical image data 500 to be a target from the list.

In step S115, the CPU 200 determines whether the medical image data 500, which has been selected in step S112, has been determined according to an operation performed by the user. If the medical image data 500 has been determined (YES in step S115), the processing proceeds to step S116. On the other hand, if the medical image data 500 has not been determined (NO in step S115), the processing proceeds to step S121. In step S116, the CPU 200 enlarges and displays the medical image data 500, which has been determined in step S115. The medical image data 500, which has been displayed on the body model 400, is contracted medical image data 500. Thus, the medical image data 500 is enlarged and displayed so that details thereof can be confirmed. A method for determining the medical image data 500 in step S115 is performed by continuously clicking the left button of the mouse on the medical image data 500 to be a target, for example. In addition, the method for determining the medical image data 500 may be performed by right-clicking the mouse in the inspected image area 303 to display the list of the medical image data 500 and selecting the medical image data 500 to be a target from the list. Needless to say, an enlargement rate of the medical image data 500 in step S116 can be optionally changed. If the entire medical image data 500 cannot be displayed, the medical image data 500 may be made movable.

In step S117, the CPU 200 determines whether the enlarged and displayed medical image data 500 has been designated according to an operation performed by the user. If the enlarged and displayed medical image data 500 has been designated (YES in step S117), the processing proceeds to step S118. On the other hand, if the enlarged and displayed medical image data 500 has not been designated (NO in step S117), the processing proceeds to step S119. In step S118, the CPU 200 stores the designated medical image data 500 in the designated image area 302. A method for designating the medical image data 500 in step S118 is performed by dragging and dropping the enlarged and displayed medical image data 500 to the designated image area 302, for example. In addition, the method for designating the medical image data 500 may be performed by right-clicking the mouse in the inspected image area 303 to display the list of medical image data 500 and selecting the medical image data 500 to be a target from the list.

As described above, according to the present exemplary embodiment, the medical image data 500 to be designated out of the plurality of medical image data 500, which has been displayed in the inspected image area 303, can be stored in the designated image area 302.

In step S119, the CPU 200 determines whether the inspected image area 303, except on the medical image data 500, has been designated. If the inspected image area 303, except on the medical image data 500, has been designated (YES in step S119), the processing proceeds to step S120. On the other hand, if the inspected image area 303, except on the medical image data 500, has not been designated (NO in step S119), the processing returns to step S116. In step S120, the CPU 200 considers that the enlarged and displayed medical image data 500 has not been designated, and ends the enlargement and display of the medical image data 500. A method for designating the inspected image area 303, except on the medical image data 500, is performed by one-clicking the right button of the mouse on the inspected image area 303, except on the medical image data 500, for example.

In step S121, the CPU 200 thumbnails all the medical image data 500 to be superimposed on the body model 400, and determines whether the medical image data 500 to be stored in the designated image area 302 has been designated out of the thumbnailed medical image data 500. If the medical image data 500 has been designated (YES in step S121), the processing proceeds to step S118. On the other hand, if the medical image data 500 has not been designated (NO in step S121), the processing ends. In other words, in the present exemplary embodiment, there are a method for designating the enlarged and displayed medical image data 500 and storing the designated medical image data 500 in the designated image area 302 and a method for designating the medical image data 500 to be stored in the designated image area 302 out of the thumbnailed medical image data 500.

In the present exemplary embodiment, the imaging site of the medical image data 500 can be intuitively confirmed from a position, on which the medical image data 500 is superimposed, on the body model 400. Even if the medical image data 500 are huge in number, the target medical image data 500 can be efficiently designated by operating the body model 400.

A second exemplary embodiment will be described below. A configuration of a medical image display apparatus according to the second exemplary embodiment is similar to the configuration illustrated in FIG. 1, and hence description thereof is not repeated. In the following description, reference numerals used in the description of the first exemplary embodiment are also diverted.

Figure 5A:
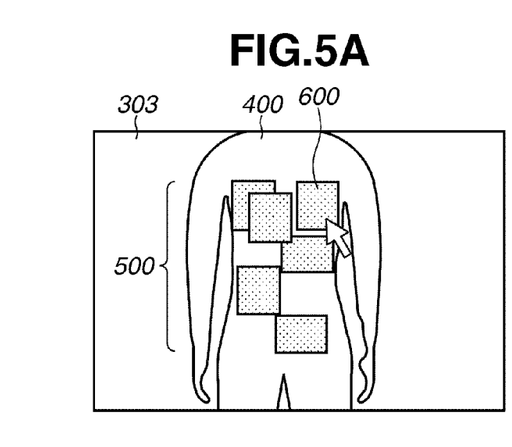
FIGS. 5A, 5B, and 5C illustrate examples of screens of an inspected image area in a second exemplary embodiment.

FIGS. 5A, 5B, and 5C illustrate examples of screens of an inspected image area 303 in the second exemplary embodiment. FIG. 5A illustrates an example of an initial screen of the inspected image area 303. In the example illustrated in FIG. 5A, an image group 600 is displayed at the left of the chest of a body model 400. The image group 600 includes a plurality of medical image data 500. If a plurality of medical image data 500 not satisfying a predetermined display criterion exists, the plurality of medical image data 500 constitutes the image group 600. If the medical image data 500 are superimposed and displayed on the body model 400 according to their priority orders, for example, the certain medical image data 500 is hidden behind the other medical image data 500, so that a predetermined ratio or more of the medical image data 500 hidden behind the other medical image data 500 may not be displayed. If there is a plurality of medical image data 500 hidden behind the other medical image data 500, the plurality of medical image data 500 constitutes the image group 600. In addition, if a plurality of medical image data 500, respective imaging sites to be set of which have not been displayed, exists, the plurality of medical image data 500 may constitute the image group 600. A type of display criterion can be optionally set according to an operation preformed by the user, and the type of display criterion is used to determine the medical image data 500 that constitutes the image group 600.

The image group 600 is displayed to be distinguishable from the medical image data 500, and is identified as an image group 600 by displaying a shadow on a back surface of the typical medical image data 500 out of the plurality of medical image data 500 constituting the image group 600. A display mode of the image group 600 is not limited to this. The image group 600 may be identified as an image group 600 by changing the type of a visible outline of the typical medical image data 500 or changing the color thereof. Any of the medical image data 500 included in the image group 600 may be selected as the typical medical image data 500. However, the medical image data 500 assigned the highest priority order out of the medical image data 500 included in the image group 600, for example, may be determined as the typical medical image data 500.

Figure 5B:
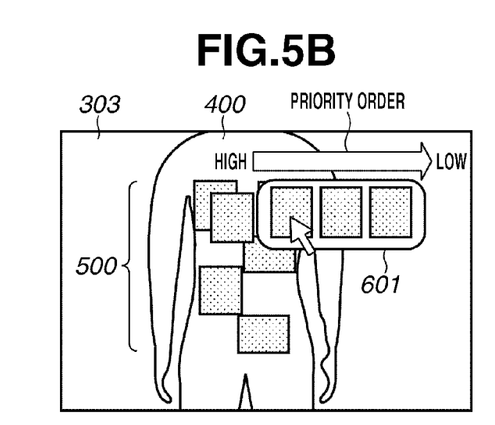

In the present exemplary embodiment, the plurality of medical image data 500 constituting the image group 600 can be list-displayed. A state 601 in FIG. 5B illustrates a state where the medical image data 500 within the image group 600 are arranged according to their respective priority orders. When thus displayed, the medical image data 500 within the image group 600 can be displayed by reflecting priority order determination items such as a display direction of the body model 400 and otherwise.

Figure 5C:
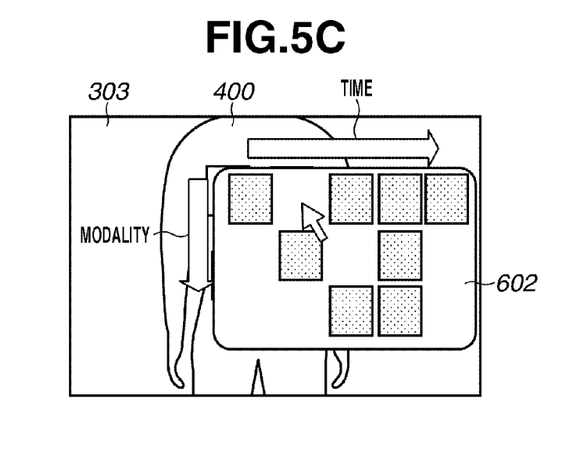

A state 602 in FIG. 5C illustrates a state where the medical image data 500 within the image group 600 are arranged in a transverse direction according to their respective imaging dates, and are arranged in a longitudinal direction according to the respective types of medical imaging apparatuses that have imaged the medical image data 500. Thus, when the medical image data 500 are compared with one another in the transverse direction, a change with time of their respective imaging sites can be seen. When the medical image data 500 are compared with one another in the longitudinal direction, the medical image data 500, which has been imaged by any of the medical imaging apparatuses, can be selected out of the medical image data 500, which have been imaged on the same date.

Figure 6A:
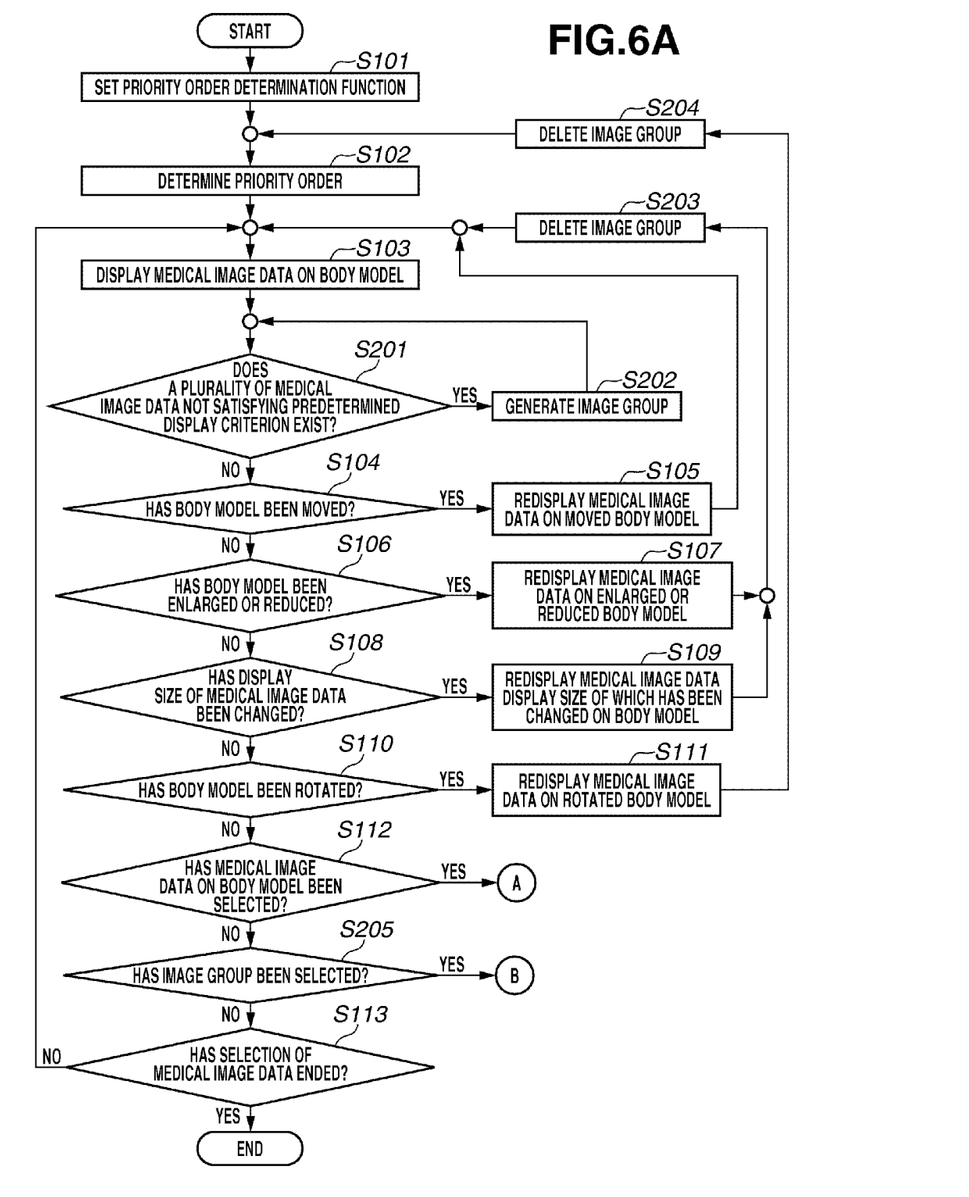
FIGS. 6A and 6B are flowcharts illustrating processing of a medical image display apparatus according to the second exemplary embodiment.
Figure 6B:
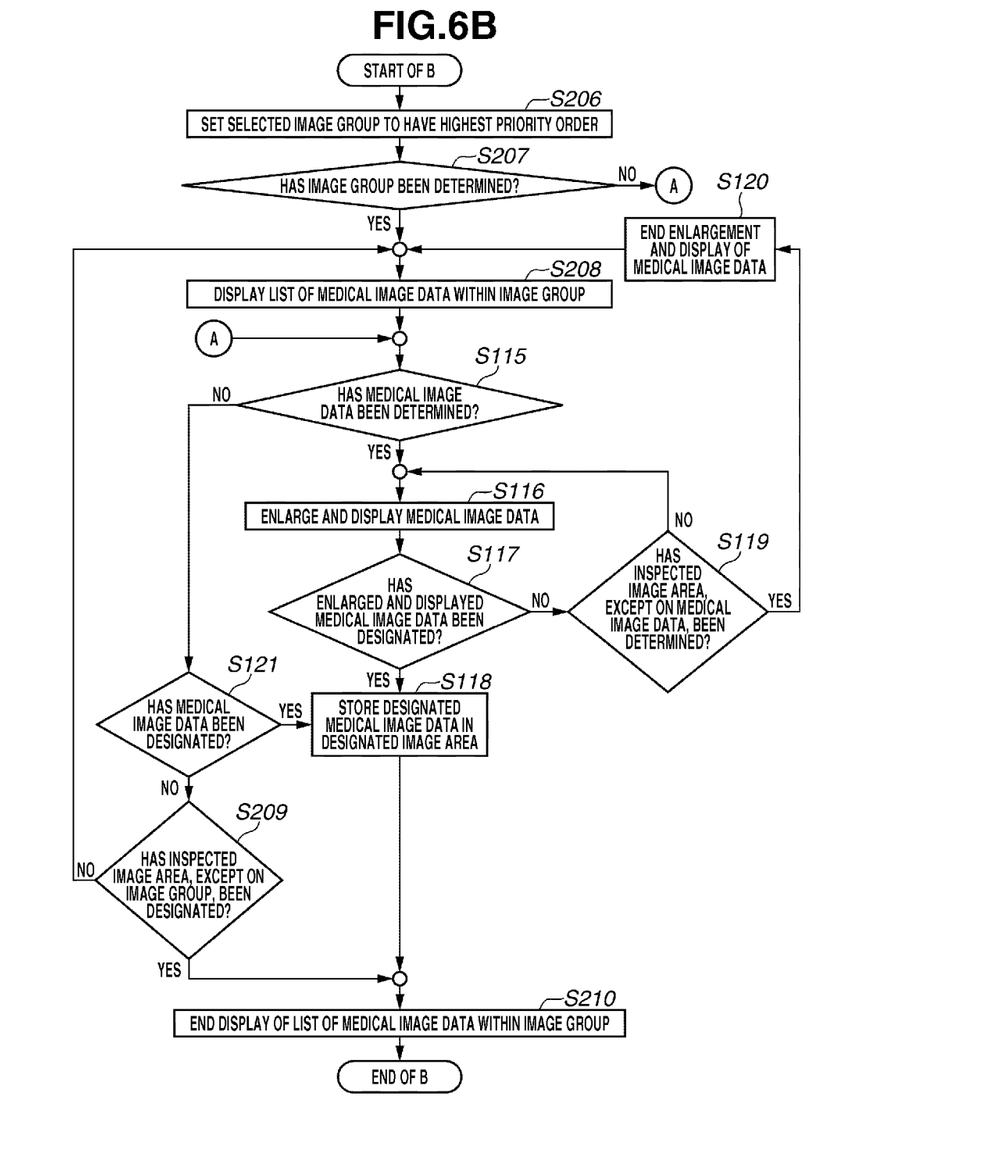

FIGS. 6A and 6B are flowcharts illustrating processing of the medical image display apparatus 10 according to the second exemplary embodiment. More specifically, FIG. 6A illustrates processing performed when a movement operation of a body model 400 has been performed, and FIG. 6B illustrates processing for medical image data 500, which has been designated in the inspected image area 303, to be stored in the designated image area 302. In FIGS. 6A and 6B, the same processing steps as those illustrated in FIGS. 4A and 4B are assigned the same reference numerals. Processing steps different from those in the first exemplary embodiment will be focused on and described below. The processing steps illustrated in FIGS. 6A and 6B are implemented when a CPU 200 reads out a required program and data from a recording medium such as a ROM 202 to a RAM 201 and executes the read program and data.

In step S201, the CPU 200 determines whether a plurality of medical image data 500 not satisfying a predetermined display criterion exists within a predetermined range. The predetermined range is a range in which a user determines that respective imaging sites of the medical image data 500 exist in the vicinity of one another and a range that can be optionally set according to an operation performed by the user. If the plurality of medical image data 500 not satisfying the predetermined display criterion does not exist (NO in step S201), the processing proceeds to step S104. On the other hand, if the plurality of medical image data 500 not satisfying the predetermined display criterion exists (YES in step S201), the processing proceeds to step S202. In step S202, the CPU 200 generates an image group 600 which is constituted by the plurality of medical image data 500 not satisfying the predetermined display criterion.

If the body model 400 has been enlarged or reduced in step S107, and if the display size of the medical image data 500 has been changed in step S109, then in step S203, the CPU 200 deletes the image group 600. If the body model 400 has been enlarged or reduced, and if the display size of the medical image data 500 has been changed, a size relationship between the body model 400 and the medical image data 500 is relatively changed. Thus, the medical image data 500 included in the image group 600 are determined according to the predetermined display criterion, and the image group 600 is reconstructed. Similarly, if the body model 400 has been rotated in step S111, then in step S204, the CPU 200 deletes the image group 600. In step S102, the CPU 200 redetermines a priority order of each of the medical image data 500 based on a display direction of the body model 400 after the rotation.

If the user has selected the medial image data 500 (YES in step S112), the processing proceeds to step S115, like in the first exemplary embodiment. On the other hand, if the user has not selected the medical image data 500 (NO in step S112), the processing proceeds to step S205. In step S205, the CPU 200 determines whether the image group 600 has been selected according to an operation performed by the user. If the image group 600 has been selected (YES in step S205), the processing proceeds to step S206. On the other hand, if the image group 600 has not been selected (NO in step S205), the processing proceeds to step S113. A method for selecting the image group 600 in step S205 is similar to the method for selecting the medical image data 500 in step S112, and differs only in that a selection target is changed from the medical image data 500 to the image group 600.

In step S206, the CPU 200 sets the image group 600, which has been selected in step S205, to have the highest priority order. Thus, the entire area of the typical medical image data 500 in the image group 600 can be displayed. In step S207, the CPU 200 determines whether the image group 600, which has been selected in step S205, has been determined according to an operation performed by the user. If the image group 600 has been determined (YES in step S207), the processing proceeds to step S208. On the other hand, if the image group 600 has not been determined (NO in step S207), the processing proceeds to step S115. A method for determining the image group 600 in step S207 is similar to the method for determining the medical image data 500 in step S115, and differs only in that a determination target is changed from the medical image data 500 to the image group 600. In step S208, the CPU 200 displays a list of the medical image data 500 within the image group 600, which has been determined in step S207.

If the processing proceeds to step S115 from step S208, then in step S115, the CPU 200 determines whether the desired medical image data 500 is determined out of the medical image data 500 within the image group 600, which have been list-displayed. If the processing proceeds to step S115 from step S112, the processing in step S115 is similar to the processing in step S115 in the first exemplary embodiment.

If the medical image data 500 has been determined (YES in step S115), the processing proceeds to step S116. In step S116, similar processing to that in the first exemplary embodiment is performed. On the other hand, if the medical image data 500 has not been determined (NO in step S115), the processing proceeds to step S121. In step S121, all the medical image data 500 to be superimposed and displayed on the body model 400 have been thumbnailed and the CPU 200 determines whether the medical image data 500 to be stored in the designated image area 302 has been designated out of the thumbnailed medical image data 500. If the medical image data 500 has been designated (YES in step S121), the processing proceeds to step S118. On the other hand, if the medical image data 500 has not been designated (NO in step S121), the processing proceeds to step S209.

In step S209, the CPU 200 determines whether the inspected image area 303, except on the image group 600, has been designated by the user. If the inspected image area 303, except on the image group 600, has been designated (YES in step S209), the processing proceeds to step S210. On the other hand, if the inspected image area 303, except on the image group 600, has not been designated (NO in step S209), the processing returns to step S208. Even after the designated medical image data 500 has been stored in the designated image area 302 in step S118, the processing proceeds to step S210. In step S210, the CPU 200 ends the display of the list of the medical image data 500 within the image group 600.

In the second exemplary embodiment, the imaging site of the medical image data 500 can be intuitively confirmed from a position, on which the medical image data 500 is superimposed, on the body model 400, like in the first exemplary embodiment. Even if the medical image data 500 are huge in number, the target medical image data 500 can be efficiently designated by operating the body model 400.

If the medical image data 500 are superimposed and displayed according to their priority orders, the medical image data 500 having the highest priority order can be confirmed. However, the other medical image data 500 are not easily confirmed. On the other hand, in the second exemplary embodiment, the medical image data 500, which are close in the imaging sites, are collected into the image group 600, and the medical image data 500 within the image group 600 can be list-displayed. Therefore, according to the second exemplary embodiment, the medical image data 500, which are close in the imaging sites, are compared with one another, and the target medical image data 500 can be easily selected.

The above-described embodiments can also implemented by performing processing for supplying software (a program) for implementing the above-described functions to a system or an apparatus via a network or various types of storage media and causing a computer (or a CPU or an MPU) in the system or the apparatus to read out and execute the program.

Advantageous Effect

According to the present disclosure, the imaging sites of the medical image data 500 can be intuitively grasped, and the required medical image data 500 can be efficiently selected.

While the present disclosure has been described with reference to exemplary embodiments, it is to be understood that these embodiments are not seen to be limiting. The scope of the following claims is to be accorded the broadest interpretation so as to encompass all such modifications and equivalent structures and functions.

This application claims the benefit of Japanese Patent Application No. 2012-220670 filed Oct. 2, 2012, which is hereby incorporated by reference herein in its entirety.

What is claimed is:

1. A medical image display apparatus comprising:
at least one memory; and
at least one processor in communication with the at least one memory, the at least one processor configured to control:
a display control unit configured to cause a display unit to display each of medical image data at a position on a body model corresponding to a respective imaging site of each of the medical image data, the medical image data including data obtained in different imaging directions, and
a determination unit configured to determine a priority order of each of the medical image data based on a display direction of the body model and an imaging direction of each of the medical image data,
wherein the display control unit causes the display unit to display each of the medical image data on the body model according to the determined priority order of each of the medical image data,
wherein the determination unit changes the priority order according to a change of the display direction of the body model by moving the body model,
wherein the determination unit determines the priority order so that, as the imaging direction gets closer to the display direction of the body model, the priority order becomes higher,
wherein the display control unit causes the display unit to redisplay each of the medical image data on the moved body model according to the changed priority order,
wherein the higher priority order the medical image data has, the larger the medical image data is displayed, and
wherein a color of the medical image data is changed according to the priority order.

2. The medical image display apparatus according to claim 1, further comprising a generation unit configured to generate an image group by a plurality of medical image data respective imaging sites of which are positioned in the vicinity of one another,
wherein the display control unit causes the display unit to display the image group generated by the generation unit on the body model.

3. The medical image display apparatus according to claim 2, wherein the generation unit generates the image group by the plurality of medical image data not satisfying a predetermined display criterion.

4. The medical image display apparatus according to claim 2, wherein the display control unit causes the display unit to display a list of the plurality of medical image data included in the image group.

5. The medical image display apparatus according to claim 4, wherein the display control unit causes the display unit to display the list of the plurality of medical image data according to respective priority orders of the plurality of medical image data.

6. The medical image data according to claim 1, wherein the determination unit further determines the priority order of each of the medical image data based on at least one of an imaging date of the medical image data, an update date of the medical image data, and a type of an apparatus that has imaged the medical image data.

7. The medical image display apparatus according to claim 1, wherein the determination unit determines the priority order of each of the medical image data based on a display direction of the body model after rotation and the imaging direction of the medical image data.

8. A medical image display method for a medical image display apparatus, the medical image display method comprising:
causing a display unit to display each of medical image data at a position on a body model corresponding to a respective imaging site of each of the medical image data, the medical image data including data obtained in different imaging directions, and
determining a priority order of each of the medical image data based on a display direction of the body model and an imaging direction of each of the medical image data,
wherein causing includes causing the display unit to display each of the medical image data on the body model according to the determined priority order of each of the medical image data,
wherein determining includes changing the priority order according to a change of the display direction of the body model by moving the body model,
wherein determining includes determining the priority order so that, as the imaging direction gets closer to the display direction of the body model, the priority order becomes higher,
wherein causing includes causing the display unit to redisplay each of the medical image data on the moved body model according to the changed priority order,
wherein the higher priority order the medical image data has, the larger the medical image data is displayed, and
wherein a color of the medical image data is changed according to the priority order.

9. A non-transitory storage medium storing a program for causing a computer to perform a medical image display method for a medical image display apparatus, the medical image display method comprising:
causing a display unit to display each of medical image data at a position on a body model corresponding to a respective imaging site of each of the medical image data, the medical image data including data obtained in different imaging directions, and determining a priority order of each of the medical image data based on a display direction of the body model and an imaging direction of each of the medical image data, wherein causing includes causing the display unit to display each of the medical image data on the body model according to the determined priority order of each of the medical image data, wherein determining includes changing the priority order according to a change of the display direction of the body model by moving the body model, wherein determining includes determining the priority order so that, as the imaging direction gets closer to the display direction of the body model, the priority order becomes higher, wherein causing includes causing the display unit to redisplay each of the medical image data on the moved body model according to the changed priority order, wherein the higher priority order the medical image data has, the larger the medical image data is displayed, and wherein a color of the medical image data is changed according to the priority order.

10. The medical image display apparatus according to claim 1, wherein the display control unit causes the display unit to display each of medical image data so that the higher priority the medical image data has, the more forward the medical image data is displayed.

11. The medical image display apparatus according to claim 1, wherein the display control unit causes the display unit to display each of medical image data so that the higher priority the medical image data has, the larger the medical image data is displayed.

12. The medical image display apparatus according to claim 1, wherein moving the body model includes rotating the body model.

13. A medical image display apparatus comprising:

at least one memory; and at least one processor in communication with the at least one memory, the at least one processor configured to control:

a display control unit configured to cause a display unit to display each of medical image data at a position on a 3-D body model corresponding to a respective imaging site of each of the medical image data, the medical image data including data obtained in different imaging directions, and a determination unit configured to determine a priority order of each of the medical image data based on a display direction of the 3-D body model and an imaging direction of each of the medical image data, wherein the display control unit causes the display unit to display each of the medical image data on the 3-D body model according to the determined priority order of each of the medical image data, wherein the determination unit changes the priority order according to a change of the display direction of the 3-D body model by moving the 3-D body model, wherein the determination unit determines the priority order so that, as the imaging direction gets closer to the display direction of the 3-D body model, the priority order becomes higher, wherein the display control unit causes the display unit to redisplay each of the medical image data on the moved 3-D body model according to the changed priority order, and wherein the higher priority order the medical image data has, the larger the medical image data is displayed.

14. A medical image display apparatus comprising:

at least one memory; and at least one processor in communication with the at least one memory, the at least one processor configured to control:

a display control unit configured to cause a display unit to display each of medical image data at a position on a 3-D body model corresponding to a respective imaging site of each of the medical image data, the medical image data including data obtained in different imaging directions, and a determination unit configured to determine a priority order of each of the medical image data based on a display direction of the 3-D body model and an imaging direction of each of the medical image data, wherein the display control unit causes the display unit to display each of the medical image data on the 3-D body model according to the determined priority order of each of the medical image data, wherein the determination unit changes the priority order according to a change of the display direction of the 3-D body model by moving the 3-D body model, wherein the determination unit determines the priority order so that, as the imaging direction gets closer to the display direction of the 3-D body model, the priority order becomes higher, and wherein a color of the medical image data is changed according to the priority order.

* * * * *